United States Patent [19]

Hino et al.

[11] Patent Number: 5,041,443
[45] Date of Patent: Aug. 20, 1991

[54] MEDICAMENT FOR TREATING CEREBRAL INSUFFICIENCY DISEASES, NOVEL 2-(1-PIPERAZINYL)-4-PHENYLCYCLOALKANOPYRIMIDINE DERIVATIVES, AND PROCESS FOR THE PRODUCTION THEREOF

[75] Inventors: Katsuhiko Hino, Nara; Naoki Kai, Amagasaki; Masato Sakamoto, Toyonaka; Tatsuya Kon, Ashiya; Makoto Oka, Ibaraki; Kiyoshi Furukawa, Shiga; Yoshiaki Ochi, Toyonaka, all of Japan

[73] Assignee: Dainippon Pharmaceutical Co., Ltd., Osaka, Japan

[21] Appl. No.: 473,414

[22] Filed: Feb. 1, 1990

[30] Foreign Application Priority Data

Feb. 21, 1989 [JP] Japan ................................. 1-40729

[51] Int. Cl.$^5$ ................. A61K 31/505; C07D 239/95; C07D 51/46
[52] U.S. Cl. ........................................ 514/254; 544/253
[58] Field of Search ...................... 544/253; 514/254

[56] References Cited

U.S. PATENT DOCUMENTS

| 3,305,553 | 2/1967 | Hoefle et al. | 260/256 |
| 3,915,976 | 10/1979 | Salmond | 544/253 |
| 4,133,884 | 1/1979 | Holmes | 514/250 |

OTHER PUBLICATIONS

Chemical Pharmaceutical Bulletin 31 (7), 2254–2261 (1983).

Primary Examiner—Mukund J. Shah
Assistant Examiner—Matthew V. Grumbling
Attorney, Agent, or Firm—Birch, Stewart, Kolasch & Birch

[57] ABSTRACT

Medicament for the treatment of cerebral insufficiency diseases comprising as an active ingredient a compound of the formula:

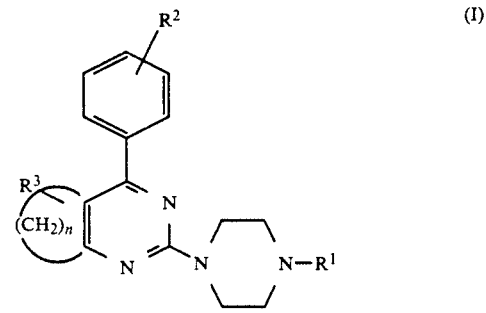

wherein n is 3, 4, 5 or 6; $R^1$ is hydrogen atom, $C_1$–$C_6$ alkyl, $C_3$–$C_8$ cycloalkyl, hydroxy-($C_2$–$C_6$) alkyl, unsubstituted or substituted aryl, heteroaryl, unsubstituted or substituted aryl-($C_1$–$C_6$) alkyl, unsubstituted or substituted arylcarbonyl-($C_1$–$C_6$) alkyl, or acyl; $R^2$ is hydrogen atom, halogen atom, $C_1$–$C_6$ alkyl, $C_1$–$C_6$ alkoxy, or trifluoromethyl; and $R^3$ is hydrogen atom or $C_1$–$C_6$ alkyl, or an acid addition salt thereof, novel 2-(1-piperazinyl)-4-phenyl-cycloalkanopyrimidine derivatives having excellent cerebral function improving activity, processes for the preparation thereof.

10 Claims, No Drawings

MEDICAMENT FOR TREATING CEREBRAL INSUFFICIENCY DISEASES, NOVEL 2-(1-PIPERAZINYL)-4-PHENYLCYCLOALKANOPYRIMIDINE DERIVATIVES, AND PROCESS FOR THE PRODUCTION THEREOF

This invention relates to novel medicament for the treatment of cerebral insufficiency diseases, novel 2-(1-piperazinyl)-4-phenylcycloalkanopyrimidine derivatives useful as an active ingredient for the treatment of the cerebral insufficiency diseases, processes for the production thereof, and a pharmaceutical composition containing the said compound as an active ingredient.

PRIOR ART

There have hitherto been known some 2-(1-piperazinyl)-4-phenylcycloalkanopyrimidine derivatives and related compounds which have pharmacological activities. For example, Japanese Patent First Publication (Kokai) No. 56-92875 discloses that 4-phenyl-2-(1-piperazinyl)quinazolines have anti-depressant activity. U.S. Pat. No. 3,305,553 discloses that 2-(4-methyl-1-piperazinyl)-4-phenylquinazolines have anti-inflammatory activity, analgesic activity and anti-allergic activity, and further discloses the starting 2-(4-methyl-1-piperazinyl)-4-phenyl-5,6,7,8-tetrahydroquinazolines but does not mention any pharmacological activity thereof.

Besides, U.S. Pat. No. 3,915,976 discloses that 2-[4-($C_1$–$C_4$)alkyl-1-piperazinyl]-4-phenyl($C_5$–$C_8$)cycloalkanopyrimidines such as 6,7,8,9-tetrahydro-2-(4-methyl-1-piperazinyl)-4-phenyl-5H-cyclohepta[d]pyrimidine and 6,7-dihydro-2-(4-methyl-1-piperazinyl)-4-phenyl-5H-cyclopenta[d]pyrimidine have anti-inflammatory activity.

Moreover, it is disclosed in Chem. Pharm. Bull., 31, 2254–2261 (1983) that 4-phenyl-2-(1-piperazinyl)-1-piperazinyl)-5,6,7,8-tetrahydroquinazoline and 4-phenyl-2-(4-benzyl-1-piperazinyl)-5,6,7,8-tetrahydroquinazoline have weak hypoglycemic activity.

However, there is no report as to the activity on the central nervous system of these 2-(1-piperazinyl)-4phenylcycloalkanopyrimidine derivatives.

BRIEF DESCRIPTION OF THE INVENTION

The present inventors have extensively searched for compounds having an activity on the central nervous system and have found that the 2-(1-piperazinyl)-4-phenylcycloalkanopyrimidine derivatives of the following formula (I) have excellent cerebral function improving activity:

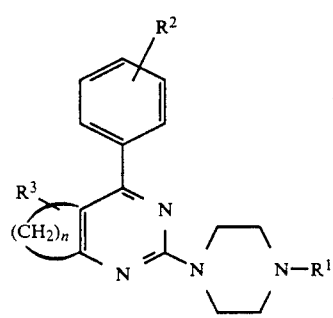

wherein n is 3, 4, 5 or 6,
  $R^1$ is hydrogen atom, $C_1$–$C_6$ alkyl, $C_3$–$C_8$ cycloalkyl, hydroxy-($C_2$–$C_6$) alkyl, unsubstituted or substituted aryl, heteroaryl, unsubstituted or substituted aryl-($C_1$–$C_6$) alkyl, unsubstituted or substituted arylcarbonyl-($C_1$–$C_6$) alkyl, or acyl,
  $R^2$ is hydrogen atom, halogen atom, $C_1$–$C_6$ alkyl, $C_1$–$C_6$ alkoxy, or trifluoromethyl,
  $R^3$ is hydrogen atom or $C_1$–$C_6$ alkyl, or an acid addition salt thereof, and further that novel compounds of the following formula (I') have particularly excellent cerebral function improving activity and are useful as an active ingredient of a cerebral function improving medicament:

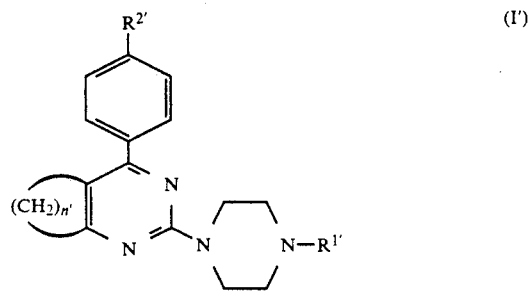

wherein n' is 3, 5 or 6; $R^{1'}$ is hydrogen, $C_1$–$C_6$ alkyl, $C_3$–$C_8$ cycloalkyl, or hydroxy-($C_2$–$C_6$) alkyl; $R^{2'}$ is hydrogen atom or fluorine atom; provided that when $R^{2'}$ is hydrogen atom, $R^{1'}$ is hydrogen atom, or an acid addition salt thereof.

An object of the invention is to provide a novel medicament for treating cerebral insufficiency diseases which comprises as an active ingredient the 2-(1-piperazinyl)-4-phenylcycloalkanopyrimidine derivatives of the formula (I). Another object of the invention is to provide novel 2-(1-piperazinyl)-4-phenylcycloalkanopyrimidine derivatives of the formula (I') which have excellent activity for treating cerebral insufficiency diseases and are useful as an agent for treating the cerebral insufficiency diseases. A further object of the invention is to provide processes for the production of the above compounds of the formula (I'). Still further object of the invention is to provide a pharmaceutical composition containing as an active ingredient the above compound of the formula (I) or (I') or a pharmaceutically acceptable acid addition salt thereof. These and other objects and advantages of the invention will be apparent to those skilled in the art from the following description.

DETAILED DESCRIPTION OF THE INVENTION

The medicament useful for the treatment of cerebral insufficiency diseases of the invention comprises as an active ingredient a 2-(1-piperazinyl)-4-phenylcycloalkanopyrimidine derivative of the formula (I), or particularly of the formula (I'), or a pharmaceutically acceptable acid addition salt thereof.

The salt of the compounds includes salts of inorganic acids (e.g. hydrochloride, hydrobromide, hydroiodide, sulfate, phosphate, etc.), and salts of organic acids (e.g. maleate, fumarate, citrate, tartrate, lactate, benzoate, methanesulfonate, etc.). Besides, these salts may optionally be present in the form of a hydrate, and hence, the compounds used in the present invention include also these hydrate compounds.

Besides, when the compounds (I) contain an asymmetric carbon, these compounds includes stereoisomers, a mixture thereof, and a racemic mixture, which are also included as the active compound in the present invention.

In the present specification and claims, the groups in the formula (I) and (I') denote the following groups.

The "alkyl" and "alkyl moiety" include straight chain or branched chain alkyl groups, for example, methyl, ethyl, propyl, isopropyl, butyl, isobutyl, pentyl, hexyl, and the like.

The "halogen atom" includes fluorine, chlorine, bromine, and iodine.

The "alkoxy" includes alkyl-O- groups wherein the alkyl moiety is methyl, ethyl, propyl, isopropyl, butyl, isobutyl, and the like.

The "unsubstituted or substituted aryl" includes aryl groups having no substituent or one or two substituents selected from halogen atom, $C_1$-$C_3$ alkyl, $C_1$-$C_3$ alkoxy, and trifluoromethyl, and the preferred examples are phenyl and 4-fluorophenyl.

The "heteroaryl" means a monocyclic or dicyclic heterocyclic group containing at least one heteroatom selected from nitrogen, oxygen and sulfur, for example, furyl, thienyl, pyridyl, isoquinolyl, and the like.

The "cycloalkyl" includes cyclopropyl, cyclobutyl, cyclopentyl, cyclohexyl, cycloheptyl, and the like.

The "hydroxyalkyl" includes 2-hydroxyethyl, 2-hydroxypropyl, 3-hyroxypropyl, 2,3-dihydroxypropyl, 4-hydroxybutyl, 2-hydroxybutyl, and the like.

The "unsubstituted or substituted arylalkyl" means alkyl groups substituted by the aryl group as mentioned above, and preferred examples are benzyl and 4-fluorobenzyl.

The "unsubstituted or substituted arylcarbonylalkyl" means alkyl groups substituted arylcarbonyl group wherein the aryl moiety is the same aryl as mentioned above, and preferred examples are 2-benzoylethyl, 3-(4-fluorobenzoyl)propyl.

The "acyl" includes, for example, formyl, acetyl, propionyl, cyclohexanecarbonyl, benzoyl, nicotinoyl, isonicotinoyl, 4-fluorobenzoyl, furoyl, thenoyl, and the like.

Among the compounds of the formula (I), preferred compounds are those of the formula (I) wherein $R^1$ is hydrogen atom, $C_1$-$C_6$ alkyl, $C_3$-$C_8$ cycloalkyl, or hydroxy-($C_2$-$C_6$) alkyl, $R_2$ is hydrogen atom or fluorine atom, and a salt thereof.

A further preferred compound as the active ingredient of the present invention is the compounds of the formula (I') or a salt thereof. Among the compounds of the formula (I'), particularly preferred compounds are the compounds of the following formula (I''):

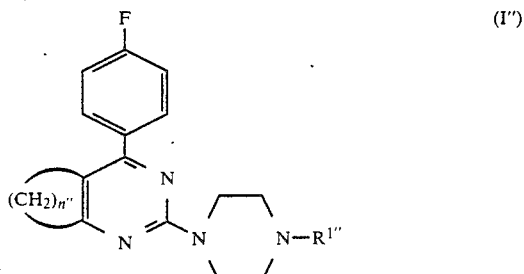

(I'')

wherein n'' is 3, 5 or 6, $R^{1''}$ is hydrogen atom, $C_1$-$C_6$ alkyl, $C_3$-$C_8$ cycloalkyl, or hydroxy-($C_2$-$C_6$) alkyl, or an acid addition salt thereof.

More preferred compounds are the compounds of the formula (I'') wherein $R^{1''}$ is hydrogen atom, $C_1$-$C_3$ alkyl, or hydroxyethyl, or an acid addition salt thereof.

The most preferred compounds in the present invention are the compounds of the formula (I'') wherein $R^{1''}$ is hydrogen atom, and a salt thereof.

Specifically preferred compounds of the present invention are as follows.

2-(1-Piperazinyl)-4-(4-fluorophenyl)-6,7-dihydro-5H-cyclopentapyrimidine 2-(1-Piperazinyl)-4-(4-fluorophenyl)-6,7,8,9-tetrahydro-5H-cycloheptapyrimidine 2-(1-Piperazinyl)-4-(4-fluorophenyl)-5,6,7,8,9,10-hexahydrocyclooctapyrimidine The compounds of the formula (I') can be prepared, for example, by the following processes.

(1) Process A

The compounds (I') are prepared by reacting a compound of the formula (II):

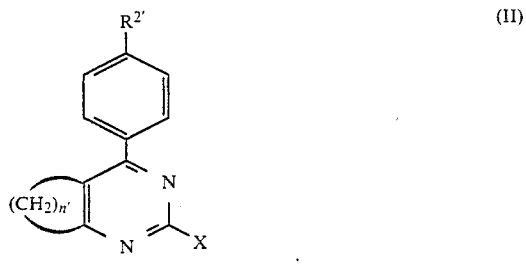

(II)

wherein X is a leaving atom or group and $R^{2'}$ and n' are as defined above, with a compound of the formula (III):

(III)

wherein $R^{1'}$ is as defined above.

The leaving atom or group X in the formula (II) denotes any atom or group which can leave off in the form of HX under the reaction conditions together with hydrogen atom bonded to the nitrogen atom at 4-position of 1-substituted piperazines. Examples of the leaving atom or group are halogen atoms, lower alkylthio groups (e.g. methylthio, ethylthio, propylthio, butylthio, etc.), arylsulfonyloxy groups (e.g. benzenesulfonyloxy, p-toluenesulfonyloxy, etc.), and alkylsulfonyloxy groups (e.g. methanesulfonyloxy, etc.).

The reaction of the compound of the formula (II) and the compound of the formula (III) is carried out in an appropriate solvent or without using any solvent. Suitable examples of the solvent are aromatic hydrocarbons (e.g. toluene, xylene, etc.), ketones (e.g. methyl ethyl ketone, etc.), ethers (e.g. dioxane, diglyme, etc.), alcohols (e.g. ethanol, isopropyl alcohol, butanol, etc.), N,N-dimethylformamide, dimethylsulfoxide. The reaction is preferably carried out in the presence of a basic substance. Suitable examples of the basic substance are alkali metal carbonates (e.g. sodium carbonate, potassium carbonate, etc.), alkali metal hydrogen carbonates (e.g. sodium hydrogen carbonate, potassium hydrogen carbonate, etc.), tertiary amines (e.g. triethylamine, but an excess amount of the compound of the formula (III) may be used instead of using the basic substance. When the compound of the formula (III) is in the form of a hydrate, the hydrate may be used. The reaction temperature is usually in the range of 40° to 200° C. The starting compound (II) can be prepared in the procedure as described in Reference Examples 1 to 29 hereinafter or in a similar process.

(2) Process B

The compounds of the formula (I') wherein $R^{1'}$ is hydrogen atom can be prepared by hydrogenolysis of a compound of the formula (I'-1):

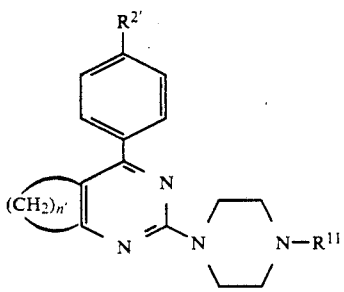

(I'-1)

wherein $R^{11}$ is unsubstituted or substituted benzyl or benzyloxycarbonyl (the substituent on the phenyl ring of said benzyl and benzyloxycarbonyl includes conventional one, such as $C_1$–$C_3$ alkyl, $C_1$–$C_3$ alkoxy, and halogen atom), and $R^{2'}$ and n' are as defined above.

The hydrogenolysis of the compounds of the formula (I'-1) is usually carried out by a conventional catalytic reduction in a solvent such as alcohols (e.g. ethanol) at room temperature under atmospheric pressure. The compounds of the formula (I'-1) can be prepared by the same process as the above-mentioned Process A. The compounds of the formula (I'-1) wherein $R^{11}$ is benzyloxycarbonyl can alternatively be prepared by a conventional process from a compound of the formula (I'-1) wherein $R^{11}$ is methyl or benzyl having optionally a substituent.

(3) Process C

The compounds of the formula (I') wherein $R^{1'}$ is hydrogen atom can also be prepared by reacting a compound of the formula (I'-2):

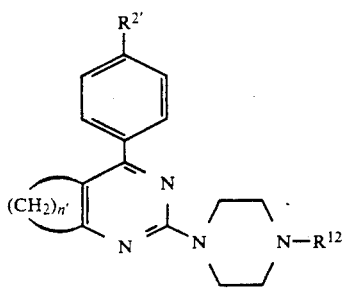

(I'-2)

wherein $R^{12}$ is methyl or unsubstituted or substituted benzyl (the substituent on the phenyl ring of the benzyl includes conventional one, such as $C_1$–$C_3$ alkyl, $C_1$–$C_3$ alkoxy or halogen atom), and $R^{2'}$ and n' are as defined above, with a chloroformic acid ester, i.e. ethyl chloroformate or 1-chloroethyl chloroformate, to give a compound of the formula (I'-3):

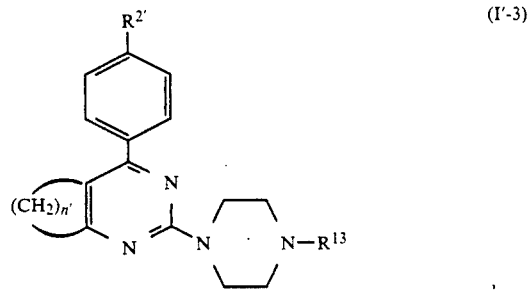

(I'-3)

wherein $R^{13}$ is ethoxycarbonyl, 1-chloroethoxycarbonyl, and $R^{2'}$ and n' are as defined above, or a compound of the formula (I'-4):

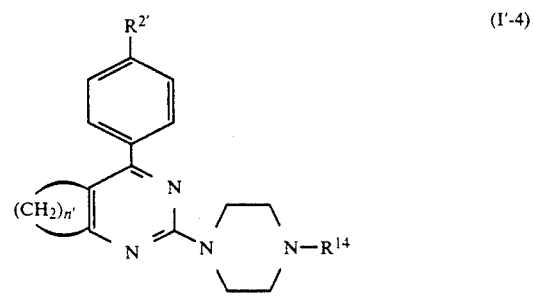

(I'-4)

wherein $R^{14}$ is acyl, and $R^{2'}$ and n' are as defined above, followed by hydrolysis of the compound of the formula (I'-3) or (I'-4).

The hydrolysis of the compound of the formula (I'-3) or (I'-4) is usually carried out by a conventional method, for example, by heating the compound in an appropriate solvent such as ethanol which is miscible with water in the presence of a basic substance (e.g. sodium hydroxide, potassium hydroxide, etc.) or an acid (e.g. hydrochloric acid, sulfuric acid, etc.). The hydrolysis of the compound of the formula (I'-3) wherein $R^{13}$ is 1-chloroethoxycarbonyl is usually carried out by heating the compound in methanol. The compounds of the formulae (I'-2) and (I'-4) can be prepared by the same process as the abovementioned Process A.

(4) Process D

The compound of the formula (I') wherein $R^{1'}$ is a group other than hydrogen atom can be prepared by reacting a compound of the formula (I'-5):

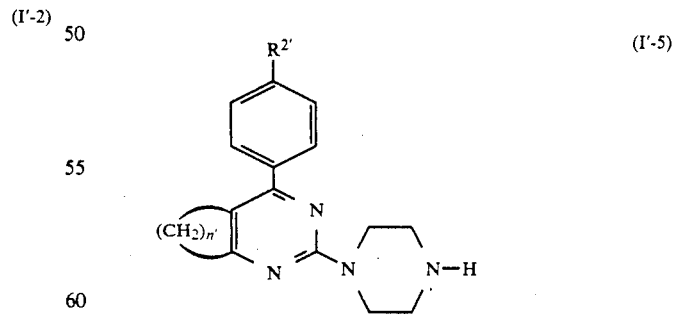

(I'-5)

wherein $R^{2'}$ and n' are as defined above, with a compound of the formula (IV):

$R^{15}$-Z          (IV)

wherein Z is a reactive residue of an alcohol, and $R^{15}$ is the same as $R^{1'}$ except hydrogen atom.

The reactive residue of an alcohol represented by the group Z includes, for example, halogen atom (e.g. chlorine, bromine, iodine, etc.), lower alkylsulfonyloxy (e.g. methanesulfonyloxy, etc.), arylsulfonyloxy (e.g. benzenesulfonyloxy, p-toluenesulfonyloxy, etc.).

The reaction of the compound of the formula (I'-5) and the compound of the formula (IV) is usually carried out in an appropriate solvent. Suitable examples of the solvent are aromatic hydrocarbons (e.g. benzene, tolune, xylene, etc.), ketones (e.g. methyl ethyl ketone, etc.), ethers (e.g. dioxane, etc.), N,N-dimethylformamide, and the like. This reaction is preferably carried out in the presence of a basic substance. The basic substance includes the same substances as used in the above Process A. The reaction temperature is usually in the range of 30° to 150° C. The compound of the formula (I'-5) can be prepared by the same processes as the above-mentioned Processes A to C.

The compounds of the formula (I) can be prepared by the same processes as mentioned above (1) to (4) or by any conventional method.

The compounds of the formula (I) or (I') can be isolated and purified from the reaction mixture by a conventional method.

The compounds of the formula (I) or (I') are obtained in the form of a free base or a salt or a hydrate depending on the kinds of the starting compound, the kinds of reaction, the reaction conditions, and the like. When the compounds are obtained in the form of a salt, they can be converted into the corresponding free base by a conventional method, for example, by treating them with a basic substance such as an alkali metal hydroxide. Besides, when the compounds are obtained in the form of a free base, they can be converted into the corresponding salt by a conventional method, for example, by treating them with various acids.

The compounds of the formulae (I) and (I') of the present invention show excellent improving effects in some animal models of memory impairment and a distinct protective effect on hypoxia-induced death in animals. The compounds also selectively bind to serotonin (5-HT$_2$) receptor and increase in concentrations of a brain serotonin metabolite (5-HIAA), or show anti-reserpine effect. Accordingly, the compounds of the present invention can be used for the treatment of various symptoms of cerebral insufficiency.

That is, the compounds of the formulae (I) and (I') of the present invention are useful as a medicament for the treatment of various symptoms of cerebral insufficiency, in dementia of Alzheimer's type, multi-infarct dementia, and other cerebrovascular dementia, and some other organic and functional brain disorders.

The compounds of the present invention which have excellent improving effects on behavioral and/or memory deficites induced by scopolamine or cycloheximide are, for example, the following compounds and a pharmaceutically acceptable salt thereof.

2-(1-Piperazinyl)-4-phenyl-6,7-dihydro-5H-cyclopentapyrimidine 2-(1-Piperazinyl)-4-(4-fluorophenyl)-6,7-dihydro-5H-cyclopentapyrimidine 2-(1-Piperazinyl)-4-phenyl-6,7,8,9-tetrahydro-5H-cycloheptapyrimidine 2-(1-Piperazinyl)-4-(4-fluorophenyl)-6,7,8,9-tetrahydro-5H-cycloheptapyrimidine 2-(1-Piperazinyl)-4-phenyl-5,6,7,8,9,10-hexahydrocyclooctapyrimidine 2-(1-Piperazinyl)-4-(4-fluorophenyl)-5,6,7,8,9,10-hexahydrocyclooctapyrimidine The compounds of the present invention which have potent selective binding to the serotonin (5-HT$_2$) receptor and have effect on increasing of concentration of brain serotonin metabolite are, for example, the following compounds and a pharmaceutically acceptable salt thereof.

2-(1-Piperazinyl)-4-(4-fluorophenyl)-6,7-dihydro-5H-cyclopentapyrimidine 2-(1-Piperazinyl)-4-(4-fluorophenyl)-6,7,8,9-tetrahydro-5H-cycloheptapyrimidine 2-(1-Piperazinyl)-4-(4-fluorophenyl)-5,6,7,8,9,10-hexahydrocyclooctapyrimidine The pharmacological activities of the representative compounds of the present invention are illustrated by the following Experiments.

EXPERIMENT 1

Antagonistic effect on scopolamine-induced hypermotility:

A group of 5 male mice (Std-ddY strain, 22–28 g) was used for examining effect of the test compounds on scopolamine-induced hypermotility, wherein the compound enhancing cholinergic neurotransmission was proved to have an antagonistic effect.

A test compound was orally administered to each mouse, and 90 minutes after the administration, each one test animal was placed within a test cage (25×35×30 cm). After 30 minutes, scopolamine hydrobromide (1 mg/kg) was intraperitoneally administered to the mice and then the motility was measured with Animex activity meter for 30 minutes. The effect of test compounds was expressed as % antagonism (complete antagonism to the motility level of non-dosed animals =100%). The results are shown in the following Table 1.

TABLE 1

| Antagonistic effect on scopolamine-induced hypermotility | | |
|---|---|---|
| Test compound | Dose (mg/kg) | Inhibitory ratio (%) |
| Ex. 1* | 3 | 60.7 |
| Ex. 2 | 30 | 69.2 |
| Ex. 3 | 3 | 68.0 |
| Ex. 4 | 10 | 66.0 |
| Ex. 5 | 30 | 81.4 |
| Ex. 6 | 30 | 64.5 |
| Ex. 7 | 30 | 78.2 |
| Ex. 8 | 10 | 80.0 |
| Ex. 9 | 10 | 60.4 |
| Ex. 10 | 3 | 50.6 |
| Ex. 12 | 30 | 80.9 |
| Ex. 13 | 30 | 97.6 |
| Ex. 14 | 3 | 55.2 |
| Ex. 16 | 30 | 54.2 |
| Ex. 17 | 30 | 72.5 |
| Ex. 18 | 30 | 54.4 |
| Ex. 19 | 3 | 64.4 |
| Ex. 20 | 30 | 35.2 |
| Ex. 21 | 30 | 70.5 |
| Ex. 23 | 30 | 52.4 |
| Ex. 24 | 30 | 72.5 |
| Ex. 25 | 10 | 67.2 |
| Ex. 26 | 30 | 59.6 |
| Ex. 27 | 30 | 42.0 |
| Ex. 28 | 30 | 96.4 |
| Ex. 29 | 30 | 59.1 |
| Ex. 30 | 30 | 75.7 |
| Ex. 31 | 10 | 61.1 |
| Ex. 32 | 30 | 62.6 |
| Ex. 33 | 30 | 42.3 |
| Ex. 34 | 30 | 50.2 |
| Ex. 37 | 30 | 62.9 |

TABLE 1-continued

Antagonistic effect on scopolamine-induced hypermotility

| Test compound | Dose (mg/kg) | Inhibitory ratio (%) |
|---|---|---|
| Ex. 38 | 30 | 81.6 |
| Ex. 39 | 30 | 55.6 |
| Ex. 40 | 30 | 64.5 |
| Ex. 41 | 30 | 60.8 |
| Ex. 42 | 30 | 71.0 |
| Ex. 43 | 30 | 64.2 |
| Ex. 45 | 30 | 60.4 |
| Ex. 46 | 30 | 100 |

*The compound of Example 1 (hereinafter, the same)

EXPERIMENT 2

Improving effect on scopolamine-induced deficit of spontaneous alternation behavior:

A group of 15-25 male mice (Std-ddY strain, 22-28 g) was used for evaluating effect of the test compounds on scopolamine-induced deficit of spontaneous alternation in a T-maze, which is a known animal model of memory impairment due to hypofunction of the cholinergic nervous system. The T-maze used consists of a stem and two arms which are 25 cm long, 5 cm wide and 10 cm high. The first 10 cm of the stem and last 10 cm of each arm are divided by sliding doors into start and goal boxes.

A test compound and scopolamine hydrobromide (1 mg/kg) were intraperitoneally administered to each mouse, and after 30 minutes a test of spontaneous alternation task in the T-maze was continuously repeated for 8 trials. Commonly, naive mice alternate each (right and left) goal box in turn, but scopolamine-treated animals tend to enter the same goal box repeatedly. The effect of the test compounds was expressed as % improvement (complete improvement to the alternation level of non-dosed mice =100%). The results are shown in Table 2.

TABLE 2

Improving effect on scopolamine-induced deficit of spontaneous alternation behavior

| Test compound | Dose (mg/kg) | Improvement (%) |
|---|---|---|
| Ex. 1* | 0.02 | 47.8 |
|  | 0.5 | 51.9 |
| Ex. 2 | 2.0 | 39.1 |
| Ex. 3 | 2.0 | 45.8 |
| Ex. 7 | 10.0 | 44.0 |
| Ex. 9 | 2.0 | 36.7 |
| Ex. 10 | 2.0 | 63.0 |
| Ex. 14 | 1.0 | 40.7 |

*The compound of Example 1 (hereinafter the same)

EXPERIMENT 3

Improving effect on cycloheximide-induced amnesia of passive avoidance response:

Anti-amnesic effect of the test compounds was examined using mice given cycloheximide which is a known amnesia-inducing agent.

A group of 15-20 male mice (Std-ddY strain, 27-33 g) was subjected to training and retention trials for a passive avoidance task in a step-down apparatus (30×30×50 cm) with a grid floor and a wooden platform (4×4×4 cm) in a center of the floor. In the training trial, each mouse was first placed on the platform, and when the mouse stepped down on the grid floor, an electric shock (1 Hz, 0.5 sec, 60 VDC) was delivered to the feet for 15 seconds. Immediately after the training trial, cycloheximide (60 mg/kg, s.c.) and a test compound (i.p.) were administered. The retention trial was carried out 24 hours thereafter, and the time from placing again each mouse on the platform until stepping down on the grid floor (step-down latency) was measured. The step-down latency in the retention trial was markedly shortened by treatment of cycloheximide (amnesia). The effect of test compounds was assessed by % improvement (complete improvement to the latency level of non-dosed animals =100 %). The results are shown in Table 3.

TABLE 3

Improving effect on cycloheximide-induced amnesia of passive avoidance response

| Test compound | Dose (mg/kg) | Improvement (%) |
|---|---|---|
| Ex. 1* | 0.5 | 33.8 |
|  | 2.0 | 65.8 |
| Ex. 2 | 0.5 | 93.7 |
|  | 2.0 | 72.8 |
| Ex. 3 | 0.5 | 34.4 |
|  | 10.0 | 52.1 |
| Ex. 7 | 0.5 | 70.4 |
| Ex. 9 | 0.5 | 85.8 |
| Ex. 10 | 0.5 | 67.1 |
| Ex. 14 | 2.0 | 52.5 |

*The compound of Example 1 (hereinafter the same)

EXPERIMENT 4

Protective effect on sodium nitrite-induced anemic hypoxia:

It is known that sodium nitrite ($NaNO_2$) induces anemic hypoxia by converting hemoglobin to metohemoglobin, resulting in a severe impairment of brain function and ultimately in death. Based on the above knowledge, prolongation of survival time after sodium nitrite treatment was used as an index for antihypoxic effect of the test compounds.

A group of 20 male mice (Std-ddY strain, 25-30 g) was intraperitoneally given a test compound (10 mg/kg), and 2 hours after the treatment with the test compound, a lethal amount (225 mg/kg) of sodium nitrite was intraperitoneally administered, and then, the survival time of each mouse was measured. The effect of the test compounds was assessed by the prolongation rate (%) of survival time compared with that of the animals treated with sodium nitrite alone.

The prolongation rate of the compound of Example 1 described hereinafter was 36.7 %.

EXPERIMENT 5

Effect of binding to dopamine ($D_2$), serotonin ($S_1$, $S_2$) and adrenaline ($\alpha_1$) receptor (in vitro receptor binding assay):

Dopamine ($D_2$), serotonin ($S_1$, $S_2$) and adrenaline ($\alpha_1$) receptor binding assays were carried out according to the methods of I. Creese et al. [Eur. J. Pharmacol., 46, 377 (1977)], S. J. Peroutka et al. [Mol. Pharmacol., 16, 687 (1979)], J. E. Leysen et al. [Mol. Pharmacol., 21, 301 (1982)], and D. C. U'Prichard et al. [Mol. Pharmacol., 13, 454 (1977)], respectively.

Crude synaptosome fractions prepared from some brain regions in rats were used as the receptor sources, and [$^3$H] spiperone ($D_2$), [$^3$H] serotonin ($S_1$), [$^3$H] ketanserin ($S_2$) and [$^3$H] WB-4101 ($\alpha_1$) were used as the labelled ligands. The binding assay was performed by incubating aliquots of synaptosome fraction in buffer solution (final volume 1 ml) containing the receptor source and the labelled ligand in the presence of a test compound having various concentration thereof for a fixed time. The assay was terminated by rapid filtration through Whatman GF/B glass fiber filters attached to a cell-harvester (Brandel) and radioactivity on the filters was counted with a scintillation counter. Specific binding was calculated as a difference between the amount of radioactivity in the assay group and that in the control group which was separately measured likewise in the presence of an excess amount of an unlabelled ligand [spiperone ($D_2$), serotonin ($S_1$), methysergide ($S_2$) and prazosin ($\alpha_1$)] instead of the labelled ligand. The $IC_{50}$ value of the test compounds (i.e. the concentration causing 50 % inhibition of the labelled ligand specific binding) was determined by probit analysis. The results are shown in Table 4.

TABLE 4

Binding effect to dopamine ($D_2$), serotonin ($S_1$, $S_2$) and adrenaline ($\alpha_1$) receptor:

| Test compound | $IC_{50}$ (nM) | | | |
|---|---|---|---|---|
| | $D_2$ | $S_1$ | $S_2$ | $\alpha_1$ |
| Ex. 1* | 920 | 750 | 29 | 1100 |
| Ex. 2 | 750 | 3000 | 9.6 | 3400 |
| Ex. 7 | 2000 | — | 38 | — |
| Ex. 10 | 130 | 1300 | 19 | 1200 |
| Ex. 28 | 350 | — | 87 | — |

*Compound of Example 1 (hereinafter, the same)

EXPERIMENT 6

Increasing effect on concentration of brain serotonin metabolite:

A group of 5 male mice (Std-ddY strain, 25-30 g) was used for examining effect of the test compounds on concentration of a brain serotonin metabolite, 5-hydroxyindole-3-acetic acid (5-HIAA). It is generally known that an increase in 5-HIAA is mainly caused by serotonin receptor blockade.

Mice were killed by decapitation two hours after the treatment with the test compounds. Brains were quickly taken out, homogenized in 1N formic acid-acetone solution, and centrifuged in a refrigerated ultracentrifuge. The supernatant was evaporated by blowing with $N_2$ gas, and then, the residue was again dissolved in 0.01N acetic acid, and served for determining 5-HIAA concentration by high performance liquid chromatography with electrochemical detection. The effect of the test compounds on 5-HIAA concentration was shown as % of control (5-HIAA level of non-dosed animals = 100%). The results are shown in Table 5.

TABLE 5

| Test compound | Increasing effect on concentration of brain serotonin metabolite | |
|---|---|---|
| | Dose (mg/kg) | 5-HIAA (%) |
| Ex. 1* | 100 | 150 |
| Ex. 2 | 100 | 135 |
| Ex. 4 | 100 | 122 |
| Ex. 5 | 100 | 161 |
| Ex. 6 | 100 | 119 |
| Ex. 14 | 100 | 154 |
| Ex. 25 | 100 | 142 |
| Ex. 27 | 100 | 131 |
| Ex. 28 | 100 | 156 |
| Ex. 29 | 100 | 149 |
| Ex. 30 | 100 | 137 |

*The compound of Example 1 (hereinafter the same)

EXPERIMENT 7

Anti-reserpine effect:

A group of 5 male mice (Std-ddY strain, 22-25 g) was used for examining the antagonistic effect of the test compounds on reserpine-induced hypothermia, which is known as a screening method for the antidepressant drug.

Reserpine (5 mg/kg) was subcutaneously administered to the mice and further a test compound was orally administered thereto. Four hours after the administration, rectal temperature of the mice was measured. The effect of the test compounds was estimated by % inhibition (complete inhibition to the hypothermia by reserpine in non-dosed animals = 100%). The results are shown in Table 6.

TABLE 6

| Test compound | Anti-reserpine effect | |
|---|---|---|
| | Dose (mg/kg) | Inhibitory ratio (%) |
| Ex. 14* | 100 | 100 |
| Ex. 25 | 100 | 63 |
| Ex. 26 | 100 | 100 |
| Ex. 27 | 100 | 46 |
| Ex. 28 | 100 | 37 |
| Ex. 30 | 100 | 67 |

*The compound of Example 14 (hereinafter the same)

EXPERIMENT 8 ACUTE TOXICITY

A group of 5 male mice (Std-ddY strain, 25-30 g) was used. The test compound (200 mg/kg) was orally administered to the test animal in the form of a 0.5% tragacanth solution or suspension, and for 7 days after the administration of the test compound, the lethality of animals was observed. As a result, no animal was died in the groups to which the test compounds of Examples 1, 2 and 9 were administered.

The compounds of the present invention can be administered either in oral route, parenteral route or intrarectal route, but preferably in oral route. The dose of the compounds may vary depending on the kinds of the compounds, administration routes, severity of the disease and age of patients, but is usually in the range of 0.01 to 50 mg/kg/day, preferably 0.01 to 5 mg/kg/day.

The compounds of the present invention are usually administered in the form of a conventional pharmaceutical preparation in admixture with a conventional pharmaceutically acceptable carrier or diluent. The pharmaceutically acceptable carrier or diluent includes the conventional pharmaceutically acceptable carriers or diluents which do not react with the compounds of the present invention. Suitable examples of the carrier or diluent are lactose, glucose, mannitol, sorbitol, dextrin, cyclodextrin, starch, sucrose, magnesium metasilicate aluminate, synthetic aluminum silicate, crystalline cellulose, sodium carboxymethyl cellulose, hydroxypropyl starch, calcium carboxymethyl cellulose, ion exchange resin, methyl cellulose, gelatin, acacia, pulluran, hydroxypropyl cellulose, low substituted hydroxypropyl cellulose, hydroxypropyl methyl cellulose, polyvinylpyrrolidone, polyvinyl alcohol, light silicic anhydride, magnesium stearate, talc, tragacanth, bentonite, veegum, carboxyvinyl polymer, titanium oxide, sorbitan fatty acid ester, sodium laurylsulfate, glycerin, glycerin fatty acid ester, anhydrous lanolin, glycerogelatin, polysorbate, macrogol, vegetable oil, wax, propylene glycol, water, and the like. The pharmaceutical preparation includes tablets, capsules, granules, fine granules, powders, syrups, suspensions, injections, suppositories, and the like. These preparations can be prepared by a conventional method. The liquid preparations may be in the form that they are dissolved or suspended in water or any other conventional medium when used. The tablets, granules and fine granules may be coated by a conventional coating agent. The injections are usually prepared by dissolving the compound of the present invention in water, but occasionally in a physiological saline solution or glucose solution, which is optionally incorporated with a buffer or a preservative. The pharmaceutical preparations may also contain other pharmaceutically active compounds.

The present invention is illustrated by the following Reference Examples, Examples and Preparations, but should not be construed to be limited thereto. The compounds are identified by elementary analysis, mass spectrum, IR spectrum, NMR spectrum, and the like.

In the Reference Examples and Examples, the following abbreviations may occasionally be used.

Et: ethyl
Me: methyl
Ph: phenyl
A: ethanol
AC: acetonitrile
D: N,N-dimethylformamide
E: diethyl ether
EA: ethyl acetate
HX: hexane
IP: isopropyl alcohol
M: methanol
MC: methylene chloride,
PE: petroleum ether Besides, the solvent shown in bracket as to the melting point in the following Reference Examples and Examples means a solvent for recrystallization.

REFERENCE EXAMPLE 1

Preparation of 4-(4-fluorophenyl)-5,6,7,8-tetrahydro-2(1H)-quinazolinone:

A mixture of 2-(4-fluorobenzoyl)cyclohexanone (14 g), urea (7.6 g), conc. hydrochloric acid (8 ml) and ethanol (40 ml) is refluxed for 8 hours. After cooling, the reaction mixture is diluted with water and washed with methylene chloride. The aqueous layer is made alkaline with potassium carbonate, and the precipitated crystal is separated by filtration and recrystallized from N,N-dimethylformamide-ethanol to give the desired compound (9.6 g), m.p. 248°-253° C.

REFERENCE EXAMPLES 2 TO 14

In the same manner as described in Reference Example 1 except that the corresponding starting materials are used, there are obtained the compounds as shown in the following Table 7.

TABLE 7

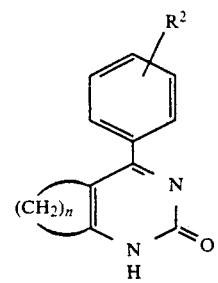

| Ref. Ex. | n | $R_2$ | Melting point (°C.) | Solvent for recrystallization |
|---|---|---|---|---|
| 2 | 3 | H | 210–215 | M-EA |
| 3 | 3 | 4-F | 210–220 | A |
| 4 | 3 | 3-F | 214–218 | M-EA |
| 5 | 3 | 4-OMe | 216–220 | M |
| 6 | 4 | H | 208–212 | A |
| 7 | 4 | 2-F | 211–216 | M-EA |
| 8 | 4 | 4-Cl | 259–268 | M-EA |
| 9 | 4 | 3-Me | 219–227 | M-EA |
| 10 | 4 | 4-CF$_3$ | 230–239 | M |
| 11 | 5 | H | 215–221 | M |
| 12 | 5 | 4-F | 252–253 | M |
| 13 | 6 | H | 253–254 | M |
| 14 | 6 | 4-F | 257–262 | A |

REFERENCE EXAMPLE 15

Preparation of 4-(4-fluorophenyl)-6-methyl-5,6,7,8-tetrahydro-2(1H)-quinazoline:

In the same manner as described in Reference Example 1 except that the corresponding starting materials are used, there is obtained the desired compound, m.p. 240°-245° C. (ethanol).

REFERENCE EXAMPLE 16

Preparation of 2-chloro-4-(4-fluorophenyl)-6,7-dihydro-5H-cyclopentapyrimidine:

To 4-(4-fluorophenyl)-1,5,6,7-tetrahydro-2H-cyclopentapyrimidin-2-one (14.3 g) is added phosphorus oxychloride (60 ml), and the mixture is refluxed for 5 hours. After cooling, the reaction mixture is diluted with chloroform (100 ml), and the mixture is added dropwise to ice-water over a period of 20 minutes. After the mixture is stirred for 30 minutes, the organic layer is separated, washed with water, dried over anhydrous sodium sulfate, and the solvent is distilled off under reduced pressure. The residue is dissolved in toluene and subjected to silica gel column chromatography. The fractions eluted with toluene are collected and the product therefrom is recrystallized from ethanol to give the desired compound (13.6 g), m.p. 106°-107° C.

REFERENCE EXAMPLES 17 TO 28

In the same manner as described in Reference Example 16 except that the corresponding starting materials are used, there are obtained the compounds as shown in Table 8.

TABLE 8

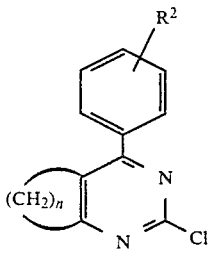

| Ref. Ex. | n | $R_2$ | Melting point (°C.) | Solvent for recrystallization |
|---|---|---|---|---|
| 17 | 3 | H | 114–115 | MC-HX |
| 18 | 3 | 3-F | 122–125 | MC-HX |
| 19 | 3 | 4-OMe | 109–110 | MC-HX |
| 20 | 4 | H | 79–80 | A-PE |
| 21 | 4 | 4-F | Oil | — |
| 22 | 4 | 4-Cl | 92–93 | MC-HX |
| 23 | 4 | 3-Me | 100 | MC-HX |
| 24 | 4 | 4-$CF_3$ | Oil | — |
| 25 | 5 | H | 118–121 | MC-HX |
| 26 | 5 | 4-F | 88–89 | HX |
| 27 | 6 | H | 108–110 | HX |
| 28 | 6 | 4-F | 124–125 | MC-HX |

REFERENCE EXAMPLE 29

Preparation of 2-chloro-4-(4-fluorophenyl)-6-methyl-5,6,7,8-tetrahydroquinazoline:

In the same manner as described in Reference Example 16 except that the corresponding starting materials are used, there is obtained the desired compound, m.p. 106°–108° C. (ethanol).

The preparation of the compounds of the formula (I') of the present invention is illustrated by the following Examples.

EXAMPLE 1

Preparation of 2-(1-piperazinyl)-4-(4-fluorophenyl)-6,7-dihydro-5H-cyclopentapyrimidine:

A mixture of 2-chloro-4-(4-fluorophenyl)-6,7-dihydro-5H-cyclopentapyrimidine (5.0 g), potassium iodide (3.3 g) and toluene (50 ml) is refluxed for 5 hours. After cooling, the reaction mixture is washed with water, dried over anhydrous sodium sulfate, and concentrated under reduced pressure. To the residue is added ethanol, and the insoluble materials are removed by filtration. To the filtrate is added a solution of maleic acid in methanol, and the resulting maleate product is recrystallized from methanol to give the maleate of the desired compound (4 g), m.p. 185°–186° C.

EXAMPLE 2

Preparation of 2-(1-piperazinyl)-4-(4-fluorophenyl)-6,7,8,9-tetrahydro-5H-cycloheptapyrimidine:

A mixture of 2-chloro-4-(4-fluorophenyl)-6,7,8,9-tetrahydro-5H-cycloheptapyrimidine (1.7 g), anhydrous piperazine (2.1 g) and dioxane (12 ml) is heated at 60° C. for 3 hours. After distilling off the solvent under reduced pressure, to the residue is added water and the mixture is extracted with chloroform. The extract is washed with water, dried over anhydrous sodium sulfate, and concentrated under reduced pressure. To the residue is added isopropyl alcohol and the insoluble materials are removed by filtration. To the filtrate is added a solution of maleic acid in ethanol, and the resulting maleate product is recrystallized from a mixture of methanol and isopropyl alcohol to give the maleate of the desired compound (1.4 g), m.p. 202°–203° C.

EXAMPLES 3 TO 15

In the same manner as described in Example 1 except that the corresponding starting materials are used, there are obtained the compounds as shown in Table 9.

TABLE 9

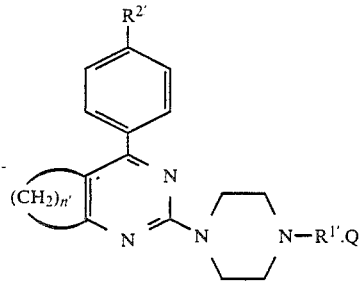

| Ex. | n' | $R^{2'}$ | $R^{1'}$ | Q | Melting point (°C.) | Solvent for recrystaln. |
|---|---|---|---|---|---|---|
| 3 | 3 | H | H | Maleate | 194–196 | A |
| 4 | 3 | F | Me | Maleate | 186–188 | A |
| 5 | 3 | F | Et | — | 121–122 | IP |
| 6 | 3 | F | $CH_2CH_2OH$ | ½ Fumarate | 203–205 | M |
| 7 | 5 | H | H | Maleate | 189–192 | M-IP |
| 8 | 5 | F | Et | Maleate | 156–158 | IP-E |
| 9 | 6 | H | H | Maleate·½$H_2O$ | 190–193 | M-A |
| 10 | 6 | F | H | Maleate | 189–191 | M-A |
| 11 | 6 | F |  | — | 131–132 | A |

TABLE 9-continued

| Ex. | n' | $R^{2'}$ | $R^{1'}$ | Q | Melting point (°C.) | Solvent for recrystaln. |
|---|---|---|---|---|---|---|
| 12 | 3 | F | cyclopentyl | — | 142–143 | A |

EXAMPLE 13

Preparation of 2-(4-n-propyl-1-piperazinyl)-4-(4-fluorophenyl)-6,7-dihydro-5H-cyclopentapyrimidine:

A mixture of 2-(1-piperazinyl)-4-(4-fluorophenyl)-6,7-dihydro-5H-cyclopentapyrimidine (1.5 g), n-propyl bromide (0.93 g), potassium carbonate (1 g), potassium iodide (0.83 g) and methyl ethyl ketone (30 ml) is refluxed for 5 hours. The reaction mixture is concentrated under reduced pressure, and the residue is dissolved in ethyl acetate. The solution is washed with water, dried over anhydrous sodium sulfate, and the solvent is distilled off under reduced pressure. The residue is dissolved in toluene, and subjected to silica gel column chromatography. The fractions eluted with ethyl acetate are collected, and thereto is added a solution of maleic acid in ethanol, and the resulting maleate product is recrystallized from ethanol to give the maleate of the desired compound (1 g), m.p. 187°–188° C.

The preparation of the compounds of the formula (I) used for the cerebral function improving medicament of the present invention other than the compounds of the formula (I') is illustrated by the following Examples.

EXAMPLE 14

Preparation of 2-(1-piperazinyl)-4-(4-fluorophenyl)-5,6,7,8-tetrahydroquinazoline:

A mixture of 2-chloro-4-(4-fluorophenyl)-5,6,7,8-tetrahydroquinazoline (2.6 g), anhydrous piperazine (4.3 g), potassium iodide (1.6 g) and toluene (40 ml) is refluxed for 5 hours. After cooling, the reaction mixture is washed with water, dried over anhydrous sodium sulfate, and concentrated under reduced pressure. To the residue is added ethanol, and the insoluble materials are removed by filtration. To the filtrate is added a solution of fumaric acid in methanol, and the resulting fumarate product is recrystallized from methanol to give the maleate ¾ hydrate of the desired compound (2.4 g), m.p. 115°–117° C.

EXAMPLES 15 to 44

IN the same manner as described in Example 14 except that the corresponding starting materials are used, there are obtained the compounds as shown in Table 10 and Table 11.

TABLE 10

| Ex. | n | $R^2$ | $R^1$ | Q | Melting point (°C.) | Solvent for recrystaln. |
|---|---|---|---|---|---|---|
| 15 | 3 | H | Et | Fumarate | 178–183 | M-A |
| 16 | 5 | H | Et | Fumarate.¼H₂O | 192–195 | M-A |
| 17 | 5 | H | Et | Fumarate.¼H₂O | 189–190 | M-A |
| 18 | 3 | H | CH₂Ph | Maleate.¼H₂O | 193–196 | E |
| 19 | 3 | 4-F | CH₂Ph | Maleate | 191–193 | A |
| 20 | 3 | 4-F | Ph | — | 153–155 | D-M |
| 21 | 3 | 3-F | Me | Fumarate | 202–207 | M-A |
| 22 | 3 | 3-F | Et | Fumarate | 186–188 | A-E |
| 23 | 3 | 4-OMe | Me | Maleate | 175–177 | M-IP |
| 24 | 3 | 4-OMe | Et | Maleate | 188–190 | M-IP |
| 25 | 4 | H | Me | Maleate | 173–176 | A |
| 26 | 4 | H | Et | Maleate | 124–127 | A |

TABLE 10-continued

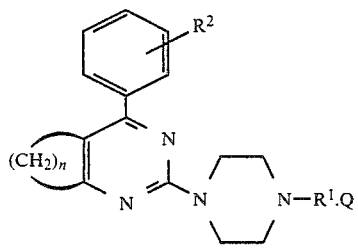

| Ex. | n | R² | R¹ | Q | Melting point (°C.) | Solvent for recrystaln. |
|---|---|---|---|---|---|---|
| 27 | 4 | H | CH₂CH₂OH | ½ Fumarate | 186–188 | M |
| 28 | 4 | 4-F | Me | Maleate | 176–177 | A |
| 29 | 4 | 4-F | Et | Maleate | 187–189 | AC |
| 30 | 4 | 4-F | CH₂CH₂OH | ½ Fumarate | 207–209 | M |
| 31 | 4 | 4-F | CH₂Ph | Maleate | 183–184 | A |
| 32 | 4 | 4-Cl | Me | Maleate | 176–178 | M-IP |
| 33 | 4 | 4-Cl | Et | Maleate | 197–199 | M-IP |
| 34 | 4 | 4-Cl | CH₂CH₂OH | HCl.½H₂O | 191–200 | IP-E |
| 35 | 4 | 4-CF₃ | H | Maleate | 195–197 | M-A |
| 36 | 4 | 4-CF₃ | Et | Maleate | 184–186 | M-A |
| 37 | 5 | H | CH₂Ph | Maleate | 210–215 | E |
| 38 | 5 | 4-F | CH₂Ph | Maleate | 204–207 | M-IP |
| 39 | 3 | 4-F | 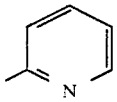 | — | 160–161 | A |

TABLE 11

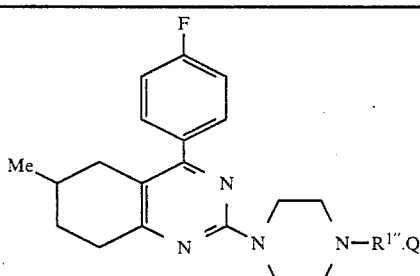

| Ex. | R¹‴ | Q | Melting point (°C.) | Solvent for recrystaln. |
|---|---|---|---|---|
| 40 | H | Maleate | 188–191 | A |
| 41 | Me | Fumarate | 190–195 | A |
| 42 | Et | Maleate | 172–173 | A |
| 43 | CH₂CH₂OH | — | 129–131 | A |
| 44 | CH₂Ph | Maleate | 202–204 | A-M |

EXAMPLE 45

Preparation of 2-[4-(2-furoyl)-1-piperazinyl]-4-(4-fluorophenyl)-6,7-dihydro-5H-cyclopentapyrimidine:

A mixture of 2-(1-piperazinyl)-4-(4-fluorophenyl)-6,7-dihydro-5H-cyclopentapyrimidine (1.0 g), 2-furoic acid (0.38 g), 1-(3-dimethylaminopropyl)-3-ethylcarbodiimide hydrochloride (0.79 g) and chloroform (40 ml) is stirred at room temperature for 2 hours. The reaction mixture is washed with water, dried over anhydrous sodium sulfate, and the solvent is distilled off under reduced pressure. The residue is dissolved in toluene, and the solution is subjected to silica gel column chromatography. The fractions eluted with toluene-ethyl acetate (9 : 1) are collected, and the product therefrom is recrystallized from ethanol to give the desired compound (0.62 g), m.p. 124°–125° C. (ethanol).

EXAMPLE 46

Preparation of 2-[4-[3-(4-fluorobenzoyl)propyl]-1-piperazinyl]-4-(4-fluorophenyl)-6,7-dihydro-5H-cyclopentapyrimidine:

In the same manner as described in Example 16 except that the corresponding starting materials are used, there is obtained a maleate of the desired compound, m.p. 168°–170° C. (ethanol).

The preparation of the pharmaceutical composition of the present invention is illustrated by the following Preparations.

Preparation 1
Preparation of capsules:

| Components | Amount |
|---|---|
| 2-(1-Piperazinyl)-4-phenyl-6,7,8,9-tetrahydro-5H-cycloheptapyrimidine maleate | 10 g |
| Corn starch | 52 g |
| Lactose | 10 g |
| Crystalline cellulose | 25 g |
| Hydroxypropyl cellulose | 2 g |
| Light silicic anhydride | 0.5 g |
| Magnesium stearate | 0.5 g |

According to a conventional method, the above components are mixed and granulated, and the granules thus obtained are packed in capsules (1000 capsules) to give capsules containing the granules of 100 mg per one capsule.

Preparation 2
Preparation of tablets:

| Components | Amount |
|---|---|
| 2-(1-Piperazinyl)-4-(4-fluorophenyl)-6,7-dihydro-5H-cyclopentapyrimidine maleate | 10 g |
| Corn starch | 15 g |
| Lactose | 30 g |
| Crystalline cellulose | 30 g |

Preparation 2
Preparation of tablets:

| Components | Amount |
| --- | --- |
| Hydroxypropyl cellulose | 5 g |
| Low substituted hydroxypropyl cellulose | 10 g |

Preparation 3
Preparation of powders:

| Components | Amount |
| --- | --- |
| 2-(1-Piperazinyl)-4-(4-fluorophenyl)-6,7,8,9-tetrahydro-5H-cycloheptapyrimidine maleate | 10 g |
| Corn starch | 168 g |
| Lactose | 300 g |
| Hydroxypropyl cellulose | 20 g |

According to a conventional method, the above components are mixed, granulated and screened, and the granules thus obtained are mixed with an appropriate amount of light silicic anhydride to give powders (50 triturations).

Preparation 4
Preparation of injections:

| Components | Amount |
| --- | --- |
| 2-(1-Piperazinyl)-4-(4-fluorophenyl)-6,7-dihydro-5H-cyclopentapyrimidine maleate | 10 g |
| D-Sorbitol | 45 g |
| 1N Aqueous solution of maleic acid or sodium hydroxide | q.s. |
| Distilled water for injection | q.s. |
| Totally | 1000 ml |

The above active ingredient and D-sorbitol are mixed with distilled water for injection, and thereto is added 1N aqueous solution of maletic acid or sodium hydroxide to adjust the solution to pH 4.0. The solution is filtered with a membrane filter (pore size, 0.22 μm) and packed in ampoule (content 10 ml). The ampoule is sealed by melting and sterilized with high pressure steam at 121° C. for 20 minutes to give injection solutions.

Preparation 5
Preparation of lyophilized preparation:

| Components | Amount |
| --- | --- |
| 2-(1-Piperazinyl)-4-(4-fluorophenyl)-6,7,8,9-tetrahydro-5H-cycloheptapyrimidine maleate | 10 g |
| D-Mannitol | 45 g |
| 1N Aqueous solution of maleic acid of sodium hydroxide | q.s. |
| Distilled water for injection | q.s. |
| Totally | 1000 ml |

The above active ingredient and D-mannitol are mixed with distilled water for injection, and thereto is added 1N aqueous solution of maleic acid or sodium hydroxide to adjust the solution to pH 4.0. The solution is filtered with a membrane filter (pore size, 0.22 μm) and packed in a vial (content 10 ml). The vial is sealed with a rubber stopper in halfway and subjected to lyophilization, that is, pre-freezing, primary drying at −50° C., secondary drying at −20° C., and then final drying at 20° C. After completely sealed with a rubber stopper within a chamber, the vial is covered with a flip-off cap to give lyophilized preparation.

What is claimed is:

1. A method for improving cerebral functions, which comprises administering a therapeutically effective amount of a compound of the formula (I):

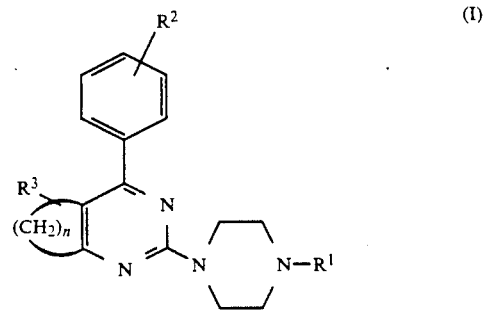

wherein n is 3, 4, 5 or 6, $R^1$ is a hydrogen atom, $C_1$–$C_6$ alkyl, $C_3$–$C_8$ cycloalkyl, hydroxy-($C_2$–$C_6$) alkyl, unsubstituted or substituted aryl, heteroaryl, unsubstituted or substituted aryl-($C_1$–$C_6$) alkyl, unsubstituted or substituted arylcarbonyl-($C_1$–$C_6$) alkyl, or acyl, $R^2$ is a hydrogen atom, halogen atom, $C_1$–$C_6$ alkyl, $C_1$–$C_6$ alkoxy, or trifluoromethyl, and $R^3$ is a hydrogen atom or $C_1$–$C_6$ alkyl, or a pharmaceutically acceptable acid addition salt thereof to a patient.

2. The method according to claim 1, wherein the active compound is a compound of the formula (I'):

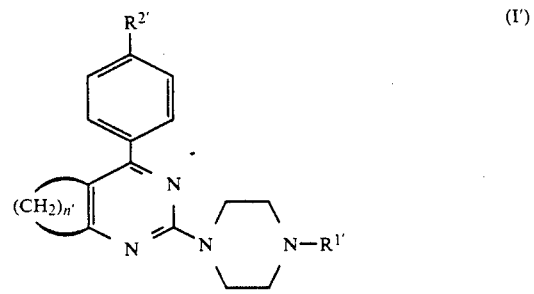

wherein n' is 3, 5 or 6; $R^{1'}$ is a hydrogen atom, $C_1$–$C_6$ alkyl, $C_3$–$C_8$ cycloalkyl, or hydroxy-($C_2$–$C_6$) alkyl; $R^{2'}$ is a hydrogen atom or fluorine atom; provided that when $R^{2'}$ is a hydrogen atom, $R^{1'}$ is a hydrogen atom, or a pharmaceutically acceptable acid addition salt thereof.

3. The method according to claim 2, wherein the compound is a compound of the formula (I') wherein $R^{2'}$ is a fluorine atom or a pharmaceutically acceptable acid addition salt thereof.

4. The method according to claim 1, wherein the method for improving cerebral functions is a method for the treatment of dementia.

5. The method according to claim 4, wherein the dementia is dementia of Alzheimer's type multi-infarct dementia or cerebrovascular dementia.

6. The method according to claim 4, wherein the active compound is a compound of the formula (I'):

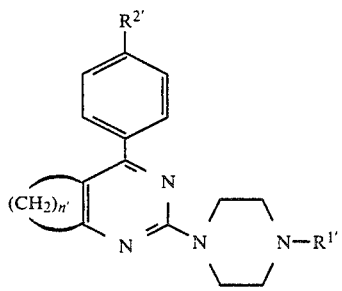
(I')

wherein n' is 3, 5 or 6; $R^{1'}$ is a hydrogen atom, $C_1$–$C_6$ alkyl, $C_3$–$C_8$ cycloalkyl, or hydroxy-($C_2$–$C_6$) alkyl; $R^{2'}$ is a hydrogen atom or fluorine atom; provided that when $R^{2'}$ is a hydrogen atom, $R^{1'}$ is a hydrogen atom, or a pharmaceutically acceptable acid addition salt thereof.

7. The method according to claim 6, wherein the compound is a compound of the formula (I') wherein $R^{2'}$ is a fluorine atom or a pharmaceutically acceptable acid addition salt thereof.

8. The method according to claim 1, wherein the method for improving cerebral functions is a method for blocking serotonin (5-$HT_2$) receptor in the brain.

9. The method according to claim 8, wherein the active compound is a compound of the formula (I'):

(I')

wherein n' is 3, 5 or 6; $R^{1'}$ is a hydrogen atom, $C_1$–$C_6$ alkyl, $C_3$–$C_8$ cycloalkyl, or hydroxy-($C_2$–$C_6$) alkyl; $R^{2'}$ is a hydrogen atom or fluorine atom; provided that when $R^{2'}$ is a hydrogen atom, $R^{1'}$ is a hydrogen atom, or a pharmaceutically acceptable acid addition salt thereof.

10. The method according to claim 9, wherein the compound is a compound of the formula (I') wherein $R^{2'}$ is a fluorine atom or a pharmaceutically acceptable acid addition salt thereof.

* * * * *